(12) United States Patent
Rajakaruna

(10) Patent No.: US 10,946,058 B2
(45) Date of Patent: Mar. 16, 2021

(54) FOOD ADDITIVES AND METHODS OF MAKING AND USING SAME

(71) Applicant: Uppala Rajakaruna, Brea, CA (US)

(72) Inventor: Uppala Rajakaruna, Brea, CA (US)

( * ) Notice: Subject to any disclaimer, the term of this patent is extended or adjusted under 35 U.S.C. 154(b) by 462 days.

(21) Appl. No.: 15/028,457

(22) PCT Filed: Mar. 26, 2014

(86) PCT No.: PCT/US2014/031834
§ 371 (c)(1),
(2) Date: Apr. 11, 2016

(87) PCT Pub. No.: WO2015/053810
PCT Pub. Date: Apr. 16, 2015

(65) Prior Publication Data
US 2016/0249663 A1    Sep. 1, 2016

Related U.S. Application Data

(60) Provisional application No. 61/889,935, filed on Oct. 11, 2013.

(51) Int. Cl.
*A61K 36/88*    (2006.01)
*A23L 33/10*    (2016.01)
*A23L 33/21*    (2016.01)
*A23L 33/22*    (2016.01)
*A23L 19/00*    (2016.01)

(52) U.S. Cl.
CPC .............. *A61K 36/88* (2013.01); *A23L 19/00* (2016.08); *A23L 33/10* (2016.08); *A23L 33/21* (2016.08); *A23L 33/22* (2016.08); *A23V 2002/00* (2013.01)

(58) Field of Classification Search
CPC ........................ A61K 36/88; A23V 2002/00
See application file for complete search history.

(56) References Cited

U.S. PATENT DOCUMENTS

| 5,112,964 A | 5/1992 | Aoe et al. |
| 6,753,019 B1 | 6/2004 | Lang et al. |
| 6,838,099 B2 | 1/2005 | Woo et al. |

FOREIGN PATENT DOCUMENTS

AU    2006233185 A1 *    5/2008    ............. A23L 19/07
WO    WO2004/069143    8/2004

OTHER PUBLICATIONS

Aziz et al. Food Chemistry 128 (2011), pp. 748-753. (Year: 2011).*
Ho et al. Food Chemistry 139 (Jan. 15, 2013), pp. 532-539. (Year: 2013).*
Kumar et al. International J of Food Sci and Technology. vol. 46, Issue 1. pp. 122-129 (Year: 2011).*
Ramakrishnan, R. Web Archive Date: Apr. 20, 2012. Retrieved from the Internet on: Aug. 23, 2019. Retrieved from: <URL: https://web.archive.org/web/20120420102953/https://simpleindianrecipes.com/BananaStemSoup.aspx>. (Year: 2012).*
(U1) "ramyas kitchen recipes". "How to clean and chop Plaintain stem". Internet date: Feb. 21, 2013. Retrieved from the Internet on: Aug. 23, 2019. Retrieved from: <URL: http://ramyaskitchenrecipes.blogspot.com/2013/02/how-to-clean-plantain-stem.html>. (Year: 2013).*
(V1) Biswas et al. International Journal of Livestock Production vol. 2(4), pp. 45-54. (Year: 2011).*
"Banana Stem Cutting and Cleaning," Dahlia, Simple Indian Recipes, (Published Feb. 8, 2016), https://simpleindianrecipes.com/Home/Banana-Stem-Cutting-Cleaning.aspx, Downloaded on Jun. 1, 2020.
Genotypic Variation in Characteristics of Nano Fibrillated Cellulose Derived from Banana Pseudostem, by Gopinathan et al. , BioResources 12(4), 6984-70001 (2017)—Not prior art.

* cited by examiner

*Primary Examiner* — Amy L Clark
(74) *Attorney, Agent, or Firm* — Enterprise Patent LLC

(57) ABSTRACT

Described herein are food additives prepared from the inner core of a banana plant stem, along with methods of making and using same.

26 Claims, No Drawings

FOOD ADDITIVES AND METHODS OF MAKING AND USING SAME

CROSS-REFERENCE TO RELATED PATENT APPLICATION

This application is a U.S. National Stage Application under 35 U.S.C. § 371 of PCT Application No. PCT/US2014/031834, filed Mar. 26, 2014, which in turn claims the benefit of priority to U.S. Provisional Application Ser. No. 61/889,935, filed Oct. 11, 2013, the entireties of which are hereby incorporated herein by reference.

FIELD OF THE DISCLOSURE

Embodiments of the present invention relate to food additives and supplements comprising tender inner core of the banana plant's trunk (banana plant stem inner tender core) fibers; methods of producing same and methods of using same in processed foods, e.g. fast food.

BACKGROUND

Obesity is a major health problem in the United States and other developed countries, where high fat diets are prevalent. In fact, a majority of the U.S. adult population is considered as overweight or obese when measured by body mass index (BMI) calculations. Additionally, over 400,000 deaths annually are attributed to obesity.

Many different approaches to deal with obesity have been proposed. Diet modifications and exercise are known to be effective, but compliance with both practices is very poor. Obesity is less prevalent among people who eat foods that are high in fiber. Fiber is a complex carbohydrate found in foods of plant origin that cannot be digested by the human body. And, while dietary fiber passes through the digestive tract unreacted, it is still an essential part of a healthy diet. In addition to preventing obesity, eating fiber rich food may reduce the risk of cancer, heart disease, diabetes, dyslipidemias and gastrointestinal disorders.

Despite the known health benefits of fiber, many people struggle to get the recommended amount of fiber through their normal diet. The palatability of fiber rich foods is at least partially responsible for this. As a result, there remains a need for fiber rich food products having an uncompromised taste profile.

Specifically, the fast food and processed food industries are continuously searching for additives which increase the fiber content of their products without compromising, inter Glia, shelf-life, compatibility with other ingredients, taste and cost.

Embodiments of the present invention are designed to meet these and other needs.

SUMMARY

Some embodiments of the present invention provide a method of preparing a food additive comprising: providing a banana plant stem; removing the outer layers of said banana plant stem to expose its inner core; soaking said inner core in an aqueous medium having a pH of from about 4 to about 7; boiling said inner core for from about 60 to 120 minutes; and drying said boiled inner core.

In some embodiments, the present invention provides a food product comprising a food additive prepared by any one of the methods described herein.

In other embodiments, the present invention provides a food additive comprising: an effective amount of the inner core of a banana plant stem; and an orally acceptable carrier.

Further embodiments provide a method of treating, preventing or inhibiting cancer, diabetes, a gastrointestinal disorder, dyslipidemia, or heart disease comprising: administering an effective amount of a food additive prepared by any one of the methods described herein, to a patient in need thereof.

DETAILED DESCRIPTION

As used herein, the term "effective amount" refers to the amount of an ingredient or component (e.g. processed inner core of a banana plant stem) required to provide a desired effect.

As used herein, the terms "processed inner core of a banana plant stem", "processed inner core", and "inner core" may be used interchangeably.

In some embodiments, the present invention provides a method of preparing a food additive comprising: providing a banana plant stem; removing the outer layers of the banana plant stem to expose its inner core; soaking the inner core in an aqueous medium having a pH of from about 4 to 7; boiling the inner core for about 60 to 120 minutes; and drying the boiled inner core. In some embodiments, the inner core is boiled in an aqueous medium. In some embodiments, the inner core is soaked and/or boiled in an acidic solution that is controlled in between a pH of 2 and 6. In some embodiments, the inner core is boiled at atmospheric pressure. In other embodiments, the inner core is boiled at elevated pressure. In still further embodiments, the inner core is boiled at elevated pressure for less than 60 minutes.

In some embodiments, the methods of the present invention further comprise cutting the inner core to an appropriate size prior to soaking the inner core in the aqueous medium.

In some embodiments, the aqueous medium in which the inner core is soaked comprises an acid selected from: acetic acid; citric acid; ascorbic acid; lactic acid; sulfuric acid; hydrochloric acid; and a combination of two or more thereof.

In some embodiments, the aqueous medium in which the inner core is boiled comprises an acid selected from: acetic acid; citric acid; ascorbic acid; lactic acid; sulfuric acid; hydrochloric acid; and a combination of two or more thereof.

In some embodiments, the aqueous medium in which the inner core is boiled further comprises a component selected from a peroxide, calcium chloride, sodium chloride, potassium chloride, sodium carbonate, sodium bicarbonate, potassium carbonate, sodium hydroxide or potassium hydroxide; and a combination of two or more thereof. In some embodiments, the aqueous medium in which the inner core is boiled comprises the ingredient in a quantity sufficient to adjust the pH of the aqueous medium in which the inner core is boiled. In some embodiments, the aqueous medium in which the inner core is boiled comprises the ingredient in a quantity sufficient to deactivate the enzyme reaction.

In some embodiments, the aqueous medium in which the inner core is soaked is maintained at a temperature of from about 40° F. to about 90° F. while the inner core is soaked. In some embodiments, the aqueous medium in which the inner core is soaked is maintained at a temperature of from about 45° F. to about 85° F. while the inner core is soaked. In some embodiments, the aqueous medium in which the inner core is soaked is maintained at a temperature of from about 50° F. to about 80° F. while the inner core is soaked. In some embodiments, the aqueous medium in which the inner core is soaked. is maintained at a temperature of from about 55° F. to about 75° F. while the inner core is soaked. In some embodiments, the aqueous medium in which the inner core is soaked is maintained at a temperature of from about 60° F. to about 70° F. while the inner core is soaked. In some embodiments, the aqueous medium in which the inner core is soaked is maintained at a temperature of about 65° F. while the inner core is soaked.

In some embodiments, the inner core is boiled at a temperature of from about 200° F. to about 250° F. In some embodiments, the inner core is boiled at a temperature of from about 205° F. to about 245° F. In some embodiments, the inner core is boiled at a temperature of from about 210° F. to about 240° F. In some embodiments, the inner core is boiled at a temperature of from about 215° F. to about 235° F. In some embodiments, the inner core is boiled at a temperature of from about 220° F. to about 230° F. In some embodiments, the inner core is boiled at a temperature of about 225° F.

In some embodiments, the methods further comprise the step of sterilizing the boiled inner core. In some embodiments, the boiled inner core is sterilized in an autoclave. In some embodiments, the boiled inner core is sterilized in an autoclave (conventional or microwave) at temperature of from about 175° F. to about 250° F. In some embodiments, the boiled inner core is sterilized in an autoclave (conventional or microwave) at temperature of from about 175° F. to about 250° F. for from about 30 to about 80 minutes.

Some embodiments further comprise the step of packing the sterilized inner core in a vessel. In some embodiments, the vessel is a bottle or a bag. In some embodiments, the vessel is hermetically sealed. The vessel can be of any shape and comprise any material that is compatible with the inner core. In some embodiments, the sterilized inner core is packed in a vessel containing a liquid medium.

In some embodiments, the inner core is dried at a temperature of from about 85° F. to about 325° F. In some embodiments, the inner core is dried at a temperature of from about 100° F. to about 300° F. In some embodiments, the inner core is dried at a temperature of from about 125° F. to about 275° F. In some embodiments, the inner core is dried at a temperature of from about 150° F. to about 250° F. In some embodiments, the inner core is dried at a temperature of from about 175° F. to about 225° F. In some embodiments, the inner core is dried at a temperature of about 200° F.

In some embodiments, the inner core is sun-dried. In some embodiments, drying of the inner core is facilitated through the use of an oven (e.g. microwave, electric or gas).

In some embodiments, the inner core is dried for from about 2 minutes to about 72 hours. In some embodiments, the inner core is dried for from about 15 minutes to about 60 hours. In some embodiments, the inner core is dried for from about 30 minutes to about 48 hours. In some embodiments, the inner core is dried for from about 45 minutes to about 36 hours. In some embodiments, the inner core is dried for from about 60 minutes to about 24 hours. In some embodiments, the inner core is dried for from about 75 minutes to about 12 hours. In some embodiments, the inner core is dried for from about 90 minutes to about 8 hours. In some embodiments, the inner core is dried for from about 120 minutes to about 6 hours. In some embodiments, the inner core is dried for from about 3 hours to about 5 hours. In some embodiments, the inner core is dried for about 4 hours.

In some embodiments, the inner core is dried to an extent sufficient to provide a water content of from about 0.01 wt. % to about 95 wt. %. In some embodiments, the inner core is dried to an extent sufficient to provide a water content of from about 0.1 wt. % to about 95 wt. In some embodiments, the inner core is dried to an extent sufficient to provide a water content of from about 0.1 wt. % to about 90 wt. %. In some embodiments, the inner core is dried to an extent sufficient to provide a water content of from about 0.5 wt. % to about 85 wt. %. In some embodiments, the inner core is dried to an extent sufficient to provide a water content of from about 1 wt. % to about 75 wt. %. In some embodiments, the inner core is dried to an extent sufficient to provide a water content of from about 2 wt. % to about 50 wt. %. in some embodiments, the inner core is dried to an extent sufficient to provide a water content of from about 3 wt. % to about 25 wt. %. In sonic embodiments, the inner core is dried to an extent sufficient to provide a water content of from about 4 wt. % to about 15 wt. %. In some embodiments, the inner core is dried to an extent sufficient to provide a water content of from about 5 wt. % to about 10 wt. %.

In some embodiments, the method further comprises the step of reducing the size of the inner core. In some embodiments, the method further comprises the step of reducing the size of the dried inner core. In some embodiments, the method further comprises the step of cutting, crushing squeezing, or grinding the inner core. In some embodiments, the method further comprises the step of granulating the dried inner core.

Some embodiments further comprise the step of washing the inner core prior to soaking the inner core.

In some embodiments, the inner core is soaked in the aqueous medium for from about 2 hours to about 8 hours. In some embodiments, the inner core is soaked in the aqueous medium for from about 2.5 hours to about 7.5 hours. In some embodiments, the inner core is soaked in the aqueous medium for from about 3 hours to about 7 hours. In some embodiments, the inner core is soaked in the aqueous medium for from about 3.5 hours to about 6.5 hours. In some embodiments, the inner core is soaked in the aqueous medium for from about 4 hours to about 6 hours. In some embodiments, the inner core is soaked in the aqueous medium for from about 4.5 hours to about 5.5 hours. In some embodiments, the inner core is soaked in the aqueous medium for about 5 hours.

In some embodiments, the method further comprises the step of mixing the inner core with a preservative.

Some embodiments provide a food product comprising a food additive described herein. Some embodiments provide a food product comprising a food additive prepared by any one of the methods described herein.

Other embodiments provide a food additive comprising: an effective amount of the inner core of a banana plant stem; and an orally acceptable carrier.

In some embodiments, the orally acceptable carrier comprises an ingredient selected from: a colorant; a preservative; a sweetener; an emulsifier; a processing aid; and a combination of two or more thereof. In some embodiments, the processing aid includes starch, colorants, preservatives, softeners, spices, salt, sugar, sugar syrups, homogenizers, emulsifiers, or enzymes.

In some embodiments, the banana stem fiber additive may have a wet, ground/pulp form that is used as a percentage of a food product. In some embodiments, the food product is a processed food product. in some embodiments, the processed food product is selected from: a pastry, pasta, a bread product, a sweet or savory filling, a sweet or savory topping, a potato product, a granola bar, a cereal bar, chili paste, pickle, soup, juice, a sauce, a chutney, a dairy product, a gravy, a pet food, a laxative, a stool softener, a batter, a coating, and a meat product. In some embodiments, the food product is selected from a donut, a muffin, a cake, a bagel, a cupcake, and a biscuit.

In some embodiments, the pastry is selected from a shortcrust pastry; a flaky pastry; a puff pastry; a choux pastry and a phyllo pastry.

In some embodiments, the bread product is selected from: a baguette, a roll, a bun, naan, pita bread, and a tortilla.

In some embodiments, the potato product is selected from: french fries; tater tots; hash browns; potato chips; and potato sticks.

In some embodiments, the meat product is selected from a fresh processed meat product; a cured meat product; a raw-cooked meat product; a precooked-cooked meat product; a raw-fermented sausage product; and a dried meat product. In some embodiments, the fresh processed meat product is selected from: hamburger; fried sausage; kebab; and chicken nuggets. In some embodiments, the cured meat product is selected from: raw-cured beef; cooked beef; cooked ham; reconstituted products; bacon; and raw ham. In some embodiments, the raw-cooked meat product is selected from: frankfurter; mortadella; lyoner and meat loaf. In some embodiments, the precooked-cooked meat product is selected from: liver sausage; blood sausage; and corned beef. In some embodiments, the raw-fermented sausage product is salami. In some embodiments, the dried meat product is selected from: biltong, beef jerky and meat floss.

In some embodiments, the food product is selected from a snack, a sweet, chocolate-based product, a biscuit, a muffin, a donut, a bagel, a cake and a cupcake.

In some embodiments, the food additive comprises from about 0.1 wt. % to about 75 wt. % of the food product. In some embodiments, the food additive comprises from about 0.5 wt. % to about 50 wt. % of the food product. In some embodiments, the food additive comprises from about 1 wt. % to about 45 wt. % of the food product. In some embodiments, the food additive comprises from about 2 wt. % to about 40 wt. % of the food product. In some embodiments, the food additive comprises from about 3 wt. % to about 35 wt. % of the food product. In some embodiments, the food additive comprises from about 4 wt. % to about 30 wt. % of the food product. In some embodiments, the food additive comprises from about 5 wt. % to about 25 wt. % of the food product. In some embodiments, the food additive comprises from about 6 wt. % to about 20 wt. % of the food product. In some embodiments, the food additive comprises from about 7 wt. % to about 15 wt. % of the food product. In some embodiments, the food additive comprises from about 8 wt. % to about 12 wt. % of the food product. In some embodiments, the food additive comprises about 10 wt. % of the food product. In some embodiments, the food additive comprises from about 0.1 wt. % to about 50 wt. % of said food product. In some embodiments, the food additive comprises from about 2 wt. % to about 25 wt. % of said food product. In some embodiments, the food additive comprises about 0.01, 0.05, 0.1, 0.2., 0.3, 0.4, 0.5, 1, 2, 3, 4, 5, 6, 7, 8, 9, 10, 11, 12, 13, 14, 15, 20, 25, 30, 35, 40, 45, 50, 55, 60, 65, 70 or 75 wt. % of the food product.

Further embodiments provide a processed food product comprising: a food additive comprising the inner core of a banana plant stem; and a meat source. In some embodiments, the meat source is selected from beef; turkey; chicken; pork; seafood; and a combination of two or more thereof.

Other embodiments provide a fresh food product comprising: a food additive comprising the inner core of a banana plant stem; and an ingredient selected from egg; flour; butter; salt; sugar; yeast; a vegetable; and a combination of two or more thereof.

Some embodiments provide a method of reducing the calorie content in a food product comprising adding an effective amount of any one of the food additives described herein to the food product. In some embodiments, the food additive replaces a carbohydrate (e.g. a starch or a sugar). In some embodiments, the food additive replaces a protein. In some embodiments, the food additive replaces a fat.

In some embodiments, the food additive serves as a carrier for delivery of flavor to the food product. Without being bound by theory, the present inventor unexpectedly discovered that the chemical structure of the inner core of the banana plant stem readily absorbs a wide variety of flavors, and can therefore be used as a delivery vehicle to flavor a food product. The use of the inner core of the banana plant stem as a delivery vehicle permits incorporation of otherwise incompatible flavors into food products.

Still further embodiments provide a method of treating, preventing or inhibiting cancer, diabetes, a gastrointestinal disorder, dyslipidemia, or heart disease comprising: administering an effective amount of any one of the food additives described herein, to a patient in need thereof.

In some embodiments, the cancer is colorectal cancer.

In some embodiments, the gastrointestinal disorder is selected from: inflammatory bowel disorders (e.g. Crohn's disease or ulcerative colitis); irritable bowel syndrome; heartburn; gastroesophageal reflux disease (GERD); Barrett's esophagus; hiatal hernia; esophagitis; ulcers; diarrhea; and constipation.

In some embodiments, the cancer is selected from colon cancer and esophageal cancer.

In some embodiments, the dyslipidemia is selected from hypercholesteremia; hypertriglyceridemia; and hyperlipoproteinemia.

The present inventor has discovered that, in some embodiments, the water content of the inner core impacts the concentration of inner core that can be used in a particular food product without undesirable effect. For example, when a dry powder or dehydrated (5-20 wt. % water content) form of processed inner core is used, it is difficult to add more than 5 wt. % of the inner core to a food product, without an impact on the taste or processibility.

Further, the processed inner core may be added to any food product, as a fiber additive replacement for protein, carbohydrate or fat. In some embodiments, the food additives described herein reduce the calorie content of a meal.

Embodiments of the present invention are designed to overcome some of the processing challenges faced by those who conducted prior work with fiber sources, e.g. enzyme reactions which result in an undesirable taste profile or decomposition of the inner core.

The invention will be described in greater detail by way of specific examples. The following examples are offered for illustrative purposes and are not intended to limit the invention in any manner. Those skilled in the art will readily recognize a variety of noncritical parameters, which can be changed or modified to yield essentially the same results.

EXAMPLES

Example 1

Fried Product

Inner core of the banana plant stem is removed by peeling off the outer layers of the stem. The inner core is washed with water and cut into pieces or shapes as desired. The inner core is soaked in acidic water solution for up to 4 hours, to prevent browning. The inner core is then washed. The inner core is then boiled for up to 8 hours depending on the final product requirement. Water is drained and the inner core is dried to an extent sufficient to provide a water content of about 80 wt. %. The dried inner core is mixed with flour and spices and deep fried.

Example 2

Bread Product

Inner core of the banana plant stem is removed by peeling off the outer layers of the stem. The inner core is washed with water and cut into pieces or shapes as desired. The inner core is soaked in acidic water solution for 6 hours, to prevent browning. The inner core is then boiled for 1-2 hours depending on the final product requirement. Water is drained and the inner core is dried to an extent sufficient to provide a water content of about 80 wt. %. ⅔ cup sugar is dissolved in a vessel containing 1 cup warm water. 1.5 tablespoons of yeast is added to the vessel. 1.5 teaspoons of salt and one quarter cup vegetable oil are added to the vessel. Six cups of white bread flour is added to the vessel one cup at time. Processed dough is kneaded on a lightly floured surface until smooth. Dough is placed in an oiled bowl to coat, and then covered with a damp cloth. Dough is allowed to rise for about 1 hour. Dough is punched down and then kneaded for a few minutes. Dough is shaped into loaves and placed into an oiled loaf pan. Dough is allowed to rise for about 30 minutes, or until dough has risen 1 inch above pan. Dough is then baked at 350° F. (175° C.) for about 30 minutes. The final product comprises about 25 wt. % processed inner core.

Table 1 (below) describes the composition of a white bread which can be made in accordance with the process described in the preceding paragraph.

TABLE 1

| Ingredient | Amount (g) |
|---|---|
| Flour | 1000 |
| Yeast | 17 |
| Brown Sugar | 22 |
| Salt | 8 |
| Processed banana stem inner core (75% water) | 900 |
| Milk | 450 |

Samples prepared with higher concentrations of inner core and/or reduced water content result in less than desirable final products. For example, a product prepared with 25 wt. % processed inner core, having a water content of 60 wt. %, fails to rise to a sufficient extent and does not deliver the desired taste profile.

Example 3

Muffin Product

Two cups all-purpose flour, one tablespoon baking powder and one-half teaspoon of salt are mixed in a first vessel. To the mixture is added processed inner core of a banana plant stem having a water content of about 90 wt. %. Beat one large egg in a second vessel and add ¼ cup granulated sugar, one cup whole milk and ½ teaspoon vanilla extract to the second vessel. Four tablespoons of melted butter is slowly mixed in with the contents of the second vessel. The contents of the first vessel are mixed gently with the contents of the second vessel. The mixture is poured into a muffin pan and baked at 400° F. for about 20 minutes. The final product comprises about 30 wt. % processed inner core.

Table 2 (below) describes the composition of an exemplary white bread product which can be made in accordance with the process described in the preceding paragraph.

TABLE 2

| Ingredient | Amount |
|---|---|
| Flour | 200 g |
| Vegetable oil | 30 g |
| Sugar | 100 g |
| Salt | 7 g |
| Baking powder | 24 g |
| Processed banana stem inner core (90% water) | 200 g |
| Milk | 100 ml |
| Egg | 1 |

Samples prepared with higher concentrations of inner core and/or reduced water content result in less than desirable final products. For example, a muffin product prepared with 30 wt. % processed inner core, but having a water content of less than 50 wt. %, results in a product that is bulky, too hard, and does not deliver the desired taste profile.

Example 4

Fast Food Meat Product

Described below in Table 3 is an exemplary fast food meat product of the present invention, which comprises the inner core of a banana plant stem, prepared according to an inventive method of the present invention.

TABLE 3

| Ingredient | Amount (g) |
|---|---|
| Meat source | 450 |
| Processed Inner Core of Banana Plant Stem (85% water content) | 450 |
| Salt | 7 |
| Pepper | 5 |
| Preservative | 0.01-0.05 |
| Egg yolk | 40 |
| Mustard | 15 |
| Chopped onion | 50 |
| Bread crumbs | 40 |
| Worcestershire sauce | 10 |

Meat products prepared with up to 40 wt. % of processed inner core of a banana plant stem (having about 90 wt. % water content) result in a product without a perceptible taste difference. However, products prepared with greater than 40 wt. % processed inner core of a banana plant stem and having a water content of less than 50 wt. %, have a more fibrous structure. The fibrous structure not only results in an undesirable taste, but the product is not stable; and once cooked, it separates into pieces.

Example 5

Fast Food Potato Product

Described below in Table 4 is an exemplary fast food potato product of the present invention, which comprises the inner core of a banana plant stem, prepared according to an inventive method of the present invention.

TABLE 4

| Ingredient | Wt. % |
| --- | --- |
| Potato source | 50-99 |
| Processed Inner Core of Banana Plant Stem | 1-50 |
| Canola oil | 0.1-0.5 |
| Dextrose | 1-5 |
| Sodium acid pyrophosphate | 0.01-0.05 |
| Citric acid | 0.01-0.05 |
| Dimethylpolysiloxane | 0.01-0.05 |
| Sodium chloride | 0.01-0.05 |

Example 6

Tortilla Chips

⅓ cup processed inner core of the banana plant stem (having a water content of about 70 wt. %) and 1 cup of corn flour are mixed. To the flour and inner core mixture is added 4.5 ounces of water. A dash of salt is added to the mixture and formed into dough. Dough is wrapped in plastic wrap and allowed to sit for about 30 minutes. Dough is rolled into eight even-sized balls and flattened. Flattened dough is then grilled on a slightly oiled skillet until golden brown. Grilled product is then cut into desired shapes, spiced as needed and baked at about 400° F., for about 10-12 minutes. The final product comprises about 30 wt. % processed inner core.

Samples prepared with higher concentrations of inner core and/or a water content of less than 50 wt. %, result in dough that is difficult to process. In addition, samples prepared with a processed inner core having a water content of greater than 80 wt. %, without an adjustment in inner core concentration, result in dough that is heavy and requires additional processing.

Example 7

Freshly Prepared Product

Add 100 grams of processed inner core having 90 wt. % water content to a vessel containing two eggs. Beat lightly and add salt and pepper to taste. Place in a warm buttered skillet on medium heat and cook for 2-3 minutes or until eggs harden to the desired extent. The final product comprises about 50 wt. % processed inner core.

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the spirit of the invention. It is intended that all such variations fall within the scope of the invention.

What is claimed is:

1. A wet banana plant stem inner core fiber food additive prepared by:

removing outer layers of a banana plant stem to provide its inner core devoid of removed outer layers;

soaking the inner core in an aqueous medium with a controlled pH between 2 and 6;

boiling the inner core for up to 8 hours in an aqueous medium with a controlled pH between 2 and 6 to produce a boiled inner core; and drying the boiled inner core to an extent sufficient to provide a water content that is from about 0.01% by weight to about 95% by weight to produce the wet banana plant stem inner core fiber food additive.

2. The wet banana plant stem inner core fiber food additive according to claim 1, wherein the aqueous medium in which the inner core is soaked is maintained at a temperature of from about 40° F. to about 90° F. while the inner core is soaked.

3. The wet banana plant stem inner core fiber food additive according to claim 1, wherein an amount of an enzyme deactivation agent is added to the boiled inner core, wherein the enzyme deactivating agent comprises: calcium chloride, sodium chloride, potassium chloride, sodium carbonate, sodium bicarbonate, potassium carbonate, sodium hydroxide, potassium hydroxide, or a combination of two or more thereof.

4. The wet banana plant stem inner core fiber food additive according to claim 1, wherein the processed inner core has a water content (moisture content) of greater than or equal to 50% by weight.

5. The wet banana plant stem inner core fiber food additive according to claim 1, wherein the inner core is cut, crushed, squeezed, ground, or granulated.

6. The wet banana plant stem inner core fiber food additive according to claim 1, wherein the inner core is mixed with a preservative.

7. The wet banana plant stem inner core fiber food additive according to claim 1, wherein the inner core is washed prior to soaking the inner core.

8. The wet banana plant stem inner core fiber food additive according to claim 1, wherein the inner core is soaked in the aqueous medium for from about 2 to about 8 hours.

9. The wet banana plant stem inner core fiber food additive according to claim 1, further comprising an orally acceptable carrier comprising an ingredient selected from a colorant, a preservative, a sweetener, an emulsifier, a processing aid, and a combination of two or more thereof.

10. The wet banana plant stem inner core fiber food additive according to claim 1, wherein a pH modifying amount of peroxide, calcium chloride, sodium chloride, potassium chloride, sodium carbonate, sodium bicarbonate, potassium carbonate, sodium hydroxide, potassium hydroxide, or a combination thereof is added after the step of boiling the inner core.

11. The wet banana plant stem inner core fiber food additive according to claim 1, further comprising a processing aid including a starch, a colorant, a preservative, a softener, a spice, a salt, a sugar, a sugar syrup, a homogenizer, an emulsifier, or an enzyme.

12. The wet banana plant stem inner core fiber food additive according to claim 1, wherein the banana plant stem fiber food additive is adapted for use in a food product containing from about 5% to about 75% by weight of banana plant stem inner core.

13. A food product made from the wet banana plant stem inner core fiber food additive according to claim 1, wherein the food product is selected from a pastry, pasta, a bakery product, bread product, a sweet or savory filling, a sweet product, a sweet or savory topping, a potato product, a granola bar, a cereal bar, chili paste, soup, juice, a sauce, a pickle, a chutney, a dairy product, a gravy, a pet food, a laxative, a stool softener, a batter, a coating, and a meat product.

14. The food product according to claim 13, wherein:
the bakery product is selected from: a muffin, a cupcake, a biscuit, a bagel, a cake, and a donut;
the sweet product is selected from a chocolate, a brownie;
the pastry is selected from a shortcrust pastry, a flake pastry, a puff pastry, a choux pastry, and a phyllo pastry;
the bread product is selected from a baguette, a roll, a bun, naan, pita bread, and a tortilla;
the potato product is selected from French fries, tater tots, hash browns, potato chips, and potato sticks; or
the meat product is selected from a fresh processed meat product, a cured meat product, a raw-cooked meat product, a precooked-cooked meat product, a raw fermented sausage product, and a dried meat product.

15. The food product according to claim 14, wherein:
the fresh processed meat product is selected from hamburger, fried sausage, kebab, and chicken nuggets;
the cured meat product is selected from raw-cured beef, cooked ham, reconstituted products, bacon, and raw ham;
the raw cooked meat product is selected from liver sausage, blood sausage, and corned beef; or
the dried meat product is selected from biltong, beef jerky, and meat floss.

16. The wet banana plant stem inner core fiber food additive of claim 1, wherein the aqueous medium for soaking or boiling comprises one of acetic acid, citric acid, ascorbic acid, lactic acid, sulfuric acid, hydrochloric acid, or a combination of two or more thereof.

17. The wet banana plant stem inner core fiber food additive of claim 1, wherein the aqueous medium for soaking comprises one of acetic acid, citric acid, ascorbic acid, lactic acid, sulfuric acid, hydrochloric acid, or a combination of two or more thereof and wherein the aqueous medium for boiling comprises one of acetic acid, citric acid, ascorbic acid, lactic acid, sulfuric acid, hydrochloric acid, or a combination of two or more thereof.

18. The wet banana plant stem inner core fiber food additive of claim 1, wherein the banana plant stem fiber food additive has a water content from about 2% by weight to about 50% by weight.

19. The wet banana plant stem inner core fiber food additive of claim 1, wherein the banana plant stem fiber food additive has a water content from about 3% by weight to about 25% by weight.

20. The wet banana plant stem inner core fiber food additive of claim 1, wherein the banana plant stem fiber food additive has a water content from about 5% by weight to about 10% by weight.

21. The wet banana plant stem inner core fiber food additive of claim 1, wherein the banana plant stem fiber food additive has a water content from about 5% by weight to about 95% by weight.

22. The wet banana plant stem inner core fiber food additive of claim 1, wherein the banana plant stem fiber food additive is employed to prepare a food product having 0.1 to 50% by weight of the banana plant stem fiber food additive.

23. The wet banana plant stem inner core fiber food additive of claim 1 wherein the banana plant stem fiber food additive is employed to prepare a food product having 10% to 25% by weight of the banana plant stem fiber food additive.

24. The wet banana plant stem inner core fiber food additive of claim 1, wherein after drying the boiled inner core, the inner core is reduced in size or is subjected to wet grinding.

25. A wet banana plant stem inner core fiber food additive prepared by:
removing outer layers of a banana plant stem to provide its inner core devoid of removed outer layers;
soaking the inner core for 2 to 8 hours in an aqueous medium with a controlled pH between 2 and 6 at a maintained temperature of from about 40° F. to about 90° F.;
boiling the inner core for up to 8 hours in an aqueous medium with a controlled pH between 2 and 6 to produce a boiled inner core; and
drying the boiled inner core from about 2 minutes to 72 hours to an extent sufficient to provide a water content that is from about 2% to about 50% by weight to produce the wet banana plant stem inner core fiber food additive.

26. The wet banana plant stem inner core fiber food additive of claim 25, wherein the banana plant stem fiber food additive is employed to prepare a food product having about 5% to 50% by weight of the banana plant stem fiber food additive.

* * * * *